Figure 1:
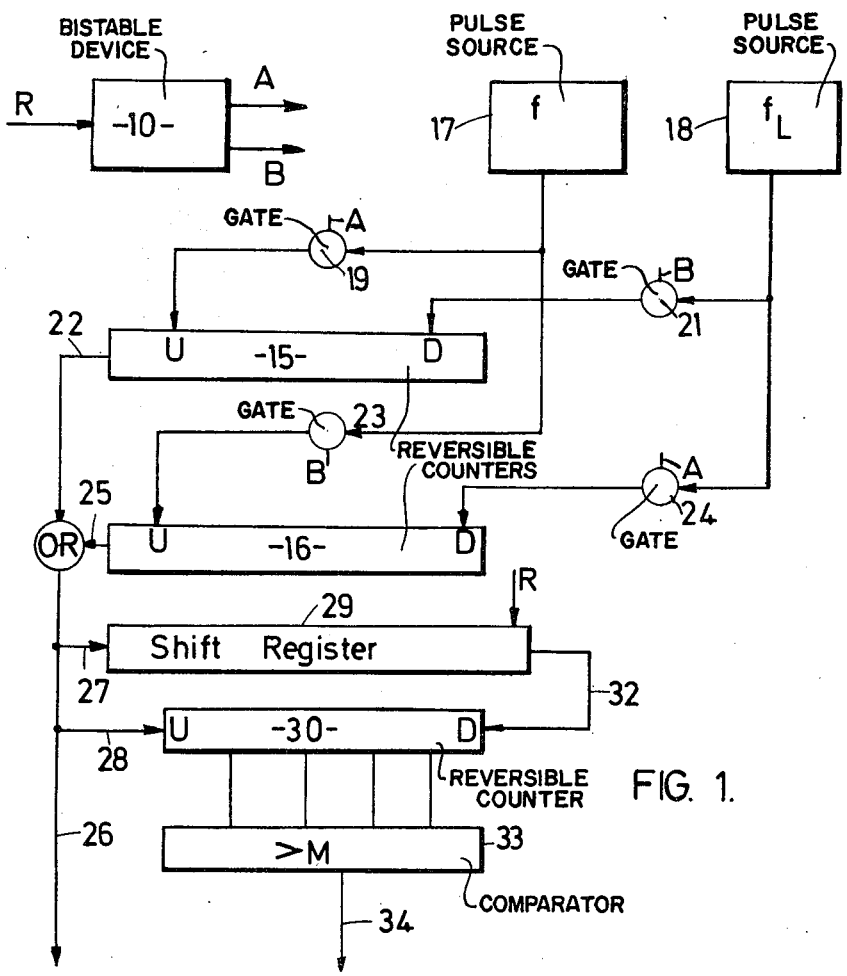

United States Patent [19]

Worstencroft

[11] 3,952,731

[45] Apr. 27, 1976

[54] CARDIAC MONITORING APPARATUS

[75] Inventor: Gerald Worstencroft, Manchester, England

[73] Assignee: Ferranti Limited, Hollinwood, England

[22] Filed: Dec. 12, 1974

[21] Appl. No.: 532,018

[30] Foreign Application Priority Data
Dec. 15, 1973 United Kingdom............... 58213/73

[52] U.S. Cl..................................... 128/2.06 A
[51] Int. Cl.² ........................................ A61B 5/04
[58] Field of Search .................. 128/2.06 A, 2.06 F, 128/2.06 R, 2.05 P, 2.05 T

[56] References Cited
UNITED STATES PATENTS

| | | | |
|---|---|---|---|
| 3,518,983 | 7/1970 | Jorgensen...................... | 128/2.06 A |
| 3,658,055 | 4/1972 | Abe et al. ...................... | 128/2.06 A |
| 3,773,038 | 11/1973 | Smith et al. ..................... | 128/2.06 F |

Primary Examiner—William E. Kamm
Attorney, Agent, or Firm—Cameron, Kerkam, Sutton, Stowell & Stowell

[57] ABSTRACT

Cardiac monitoring apparatus comprises means for detecting normal and/or ectopic complexes in an electrocardiogram waveform, means for comparing the intervals between successive detected complexes, and means for detecting that successive said intervals differ by more than a predetermined amount. Reversible counters are used in pairs with different counting rates for the counters of each pair to perform the comparing and detecting. Preferably the monitoring apparatus further comprises shifting means arranged to be clocked once for each electrocardiogram complex, whether ectopic or not, and operative to store ectopic indications, and means for indicating that, at any one time, the shift register means contains more than a predetermined number of ectopic indications.

9 Claims, 3 Drawing Figures

CARDIAC MONITORING APPARATUS

The invention relates to monitoring heart activity.

A significant sustained increase of heart beat rate in a person with known or suspected heart problems may lead to fibrillation in which the heart trembles without pumping. A significant sustained decrease of heart beat rate may lead to heart stoppage. These two sustained conditions precedent to heart failure are fairly easy to detect as predetermined percentage variations of a particular patient's normal heart beat rate, for example when the heart beat goes above or below predetermined rates. Provision for audible and/or visual warning is often made for these conditions, e.g. in an intensive cardiac care unit of a hospital. There is another heart beat condition that needs to be watched for and which is not a sustained condition. This is the occurrence of ectopics which may be considered as discrete "false" or abnormal beats and are usually detected because of differences of shape in an electrocardiogram when compared with waveform complexes associated with normal beats. In an intensive care unit, ectopics detection is often done by having nurses continuously watching electrocardiogram waveforms on the screen of a visual display unit. Such a screen will normally show waveforms for several patients simultaneously and the task of watching them is both demanding and tedious. Proposals for automatically detecting ectopic complexes have been made based on their being of abnormal shape compared with normal heat beat complexes. Such techniques tend to be complex and expensive and may miss any ectopic complex that closely resembles a normal complex.

It is an object of this invention to facilitate the detection of ectopics without relying wholly on waveform shape comparisons.

As ectopics often correspond to action independent of normal heart beat activity their occurrence is likely not to coincide with the time of an expected normal beat, and this invention aims to exploit the differences of time intervals between detected complexes in order to identify ectopics. It has been found that the interval to a normal heart beat from a preceding ectopic very often is comparatively long due to unavoidable recovery time after the ectopic spasm.

According to one aspect of the invention there is provided a cardiac monitor comprising means for detecting normal and/or ectopic complexes in an electrocardiogram waveform, means for comparing the intervals between successive detected complexes, and means for detecting that successive such intervals differ by more than a predetermined amount.

Conveniently, the means for detecting complexes includes a bistable device switchable between its states by each said complex.

The means for comparing may comprise reversible binary counting means arranged for counting in different directions during successive said intervals at different rates, occurrence of predetermined states of the counting means producing outputs representing successive intervals of durations differing by amounts greater than accounted for by differences between the counting rates.

In one embodiment a pair of reversible counters are each arranged for counting in opposite directions relative to each other, one direction being at a first rate and the other direction being at a second rate, and the counters both being reversed on occurence of each said complex.

Such apparatus will detect single ectopic complexes not occurring simultaneously with an expected normal complex irrespective of their shape. This is important as extra heart activity may result in complexes that are similar to at least the central section of a normal complex that previous proposals have tended to use for shape comparison purposes with the often true presumption that ectopics will be significantly larger or smaller.

Ectopics may occur in rapid succession and such apparatus may detect the first ectopic or the last ectopic of a sequence depending on whether the reversible counters have the frequencies applied so as to detect that one interval is shorter or longer than the immediately succeeding interval. The provision of a further pair of reversible counters with frequencies applied so as to detect the opposite relation between successive intervals will result in both the first and the last of a sequence of ectopics being detected. Provision of a gate enabled by the first ectopic and disabled by the last ectopic will allow any intervening complexes to be counted as ectopics.

In addition to identifying individual ectopics it is often desired to know their frequency of occurrence.

According to another aspect of the invention there is provided a cardiac monitor for providing indications of ectopics, and including shift register means clocked once for each complex of a received electrocardiogram and operative to store ectopic indications, and means for indicating that, at any one time, the shift register means contains more than a predetermined number of ectopic indications.

Such apparatus has the advantage of measuring ectopics as a proportion of total detected normal and ectopic complexes in an electrocardiogram rather than a simple count over a set period of time, and so is not sensitive to the considerable differences of heart beat rate that naturally occur from patient to patient.

Figure 2:
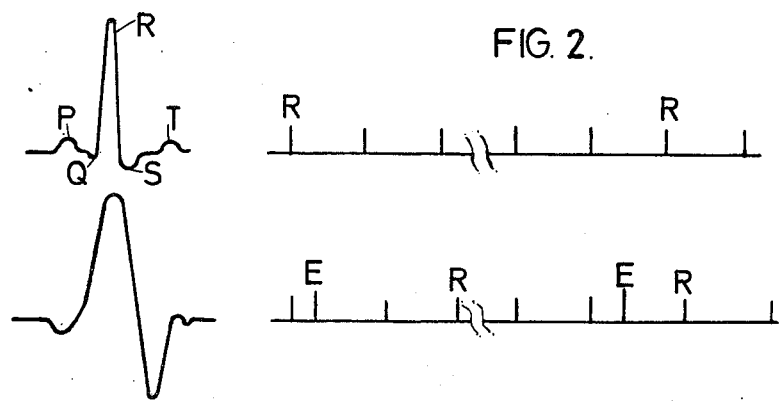
Figure 3:
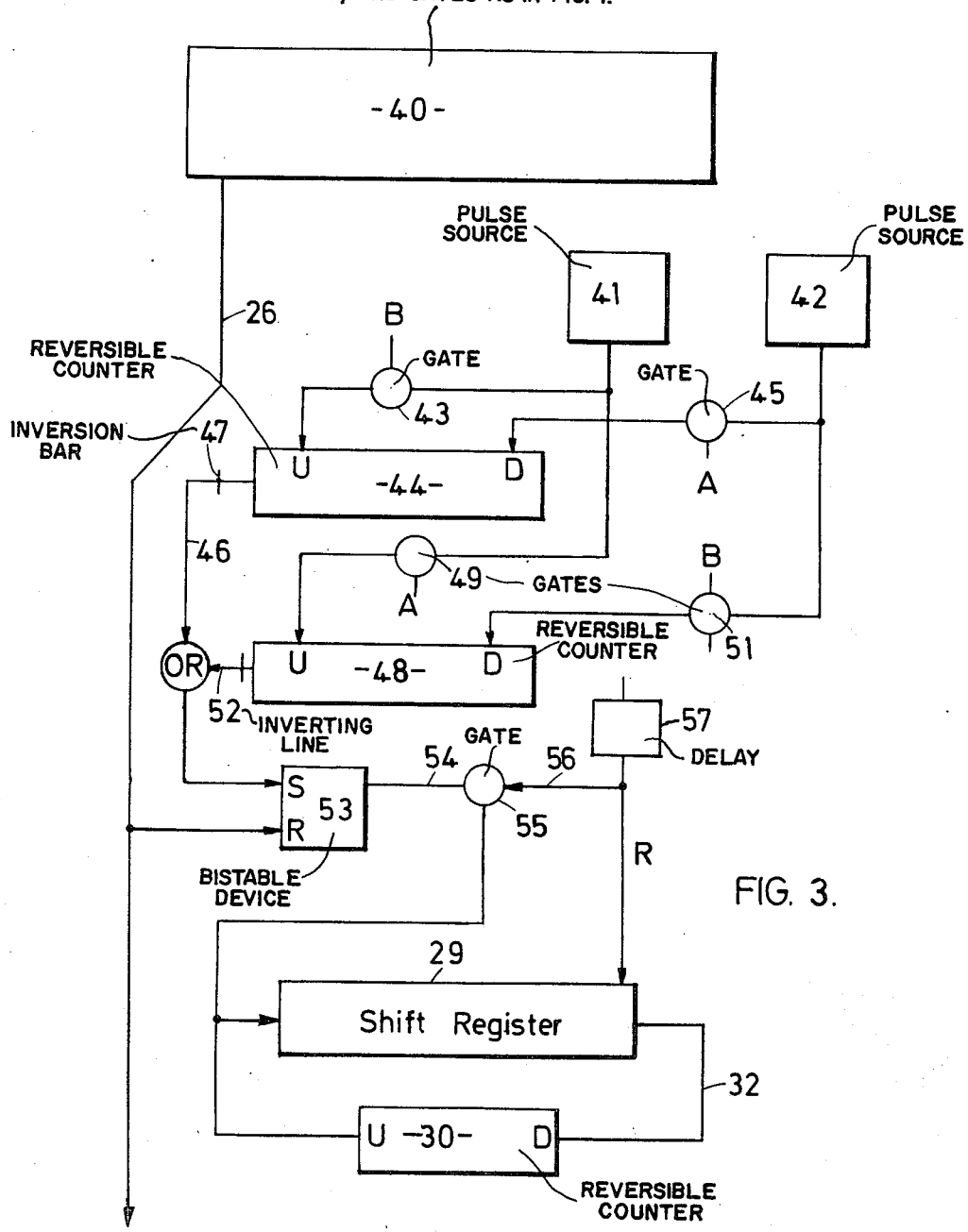

Embodiments of the invention will now be specifically described, by way of example, with reference to the accompanying drawings in which:

FIG. 1 is a block circuit diagram of apparatus for detecting single ectopic complexes in an electrocardiac waveform;

FIG. 2 gives a general indication of a natural heart beat complex and one type of ectopic complex that may occur in an electrocardiac waveform and also indicates repetition intervals of waveforms with and without ectopic complexes; and FIG. 3 is a block circuit diagram of apparatus similar to FIG. 1 but also relating to means for detecting a sequence of ectopic complexes.

In FIG. 1, pulses representing the presence of normal and/or ectopic complexes in an electrocardiac waveform are applied at R to a bistable device 10, for example a J–K flip flop, responsive to each pulse to switch its state. The device 10 has complementarily energised outputs A and B each capable of two voltage levels between which it is switched as the bistable device 10 changes state. These outputs A and B will therefor each alternate in voltage levels for successive intervals between R pulses and will always be at different levels relative to each other.

The input pulses to the bistable device 10 are referenced 'R' in deference to conventional consideration of the various parts of a normal heart beat waveform which, as shown at the start of the first line of FIG. 2, has its major excursion labelled R. This major excursion is part of the central QRS portion of the heart beat waveform complex which results from depolarisation of the ventricles of the heat on contraction. The QRS portion is preceded by a small pulse, the P-wave, signifying initiation of muscular activity, and succeeded by another small pulse, the T-wave, signifying the start of muscle relaxation. It is easy to detect the R excursion of the QRS portion which is generally much greater than other excursions. A sequence of regularly appearing heart beats is indicated in the remainder of the first line of FIG. 2 with substantially constant intervals as would be expected from a normal healthy heart in a rest situation.

In practice, the R pulses for input to the bistable 10 are generated of acceptable amplitude, and fixed duration and polarity voltage excursions irrespective of actual ECG complex variations. An appropriate amplifier and pulse generator or shaper will be used.

The outputs A and B of the bistable device 10 are used to control gating of pulses to a pair of reversible counters 15 and 16. Two pulse sources 17 and 18 are used both of which have repetition rates that are fast relative to maximum heart-beat but one of which, 17, exceeds the other, 18 by a desired percentage set to exclude the effects of heart beat rate changes acceptable as normal in the known circumstances of the patient. For this purpose, either, or each, of the pulse sources 17 and 18 has a variable repetition rate, thereby allowing detection of successive pulse intervals that differ in duration by more than an amount corresponding to the frequency relation of the pulse sources 17 and 18.

The reason for this is demonstrated in the second line of FIG. 2, which shows an abnormal waveform complex which may denote abnormal ventricular action corresponding to one type of ectopic. Such activity is not necessarily related to normal heart beat activity, i.e., it is not merely a distorted QRS portion of a regularly appearing heart beat. Rather, it is extra activity whose occurrence is largely independent of normal heart pumping action so that such ectopic complexes will appear in an electrocardiogram as additional pulses between normal heart beat complexes — at least in the early stages of a deteriorating condition of the patient when they are infrequent and thus difficult to spot without devoting highly competent personnel full-time. The occurrence of an ectopic will, of course, often have some effect on the time relation of the next normal beat relative to the immediately preceding normal beat. It will, however, almost always produce a shorter than normal interval from the preceding normal heart beat to the start of the ectopic. The remainder of the second line of FIG. 2 shows the occurrence of ectopic relatively close to the preceding normal heart beat.

The apparatus of FIG. 1 detects the occurrence of a shorter interval followed by a longer (normal) one. The counter 15 is controlled by gate 19 to count up when the bistable device 10 is in a state where the voltage on its output A enables the gate 19 to pass the higher rate pulses from pulse generator 17 to the up-count terminal U. The next R pulse will switch the bistable device 10 and disable the gate 19. The bistable device output B will then enable gate 21 to pass lower frequency pulses from pulse generator 18 to the down-count terminal D of the counter 15. It is assumed that the counter 15 is reset each time the bistable 10 switches to the state where its output A is at the gate enabling voltage. This may be done by gating the R pulse to the appropriate counter reset terminal whenever the A output is in its gate enabling condition.

The counter 15 will be decremented through zero only if the time interval, say $n$th, for which gate 21 is enabled exceeds the preceding time interval by an amount such that the ratio of the two intervals $(n\text{th}/(n-1)\text{th})$ exceeds that of the higher frequency (17) to the lower frequency (18). If this happens a borrow line from the counter 15 will change state and can be utilised to operate an alarm or a counter or both, as desired.

In effect the bistable 10 and counter 15 are operative to split the intervals between the R pulses into non-overlapped consecutive pairs and compare the intervals of each pair to see if the second one is longer by a predetermined amount.

The second counter 16 is used to do a similar comparison for pairs of consecutive intervals that overlap those tested by the first counter 15. To this end it is connected via gates 23 and 24 enabled by bistable outputs B and A, respectively, to count up on the higher rate pulses and down on the lower rate pulses when the first counter 15 is doing the opposite. The counter 16 thus tests those intervals bridging the interval pairs tested by counter 15 and will energise its borrow line 25 when the interval ratio indicates an ectopic.

The borrow lines 22 and 25 of the counters 15 and 16 are OR-ed together to form an ectopic alarm output on line 26. Such a system will detect all single ectopic complexes for which the interval is short enough compared with the normal interval as determined by the pulse frequency ratio.

In general, it is desired to know what proportion of total complexes in the electrocardiogram are ectopics. A significant increase in that proportion, or achievement of a particular level, may indicate a specially noteworthy condition. To achieve this the ectopic indicating line 26 is branched at 27 and 28 as inputs to a shift register 29 and up-count input to a reversible counter 30. The shift register 29 is clocked by the R pulses that feed the bistable device 10 and its output 32 is fed to the decrement terminal of the reversible counter 30. The counter 30 will therefore represent by its contents the number of ectopics that occur in whatever number of R pulses equals the number of stages of the shift register 29. The simplest alarm system would use the carry output of the counter as a further alarm signal. However, it is preferred to use a presettable comparator 33 fed with the contents of the counter 30 and operative to give an output 34 whenever the counter contents exceed a preset number say M. A shift register capacity of 400 stages and a maximum counter capacity of 15 have been found to be particularly useful.

The output 34 of the counter 33 may be used to gate a further counter for measuring the total time during which the proportion of ectopics exceeds the number M. Alternatively or additionally, it may be connected to a visual and/or audible alarm.

Sometimes ectopics occur in bursts, i.e., several will occur in sequence with substantially similar intervals relatively short compared with normal heart beat intervals. Usually such bursts are not sustained for long enough to activate any warning system that may be provided to cope with sustained significant changes of heart beat frequency. The above described system of FIG. 1 will detect only the last one of such a burst of ectopic complexes. It is desirable to add a facility for detecting the first ectopic of such a burst and for registering intervening ones. Such a facility is shown in FIG. 3.

In the system of FIG. 1, a shorter interval preceding a longer one is detected by counting up at one rate during the second interval. The opposite case of a shorter interval following a longer one can be detected by the inverse arrangement involving counting up during the first interval slower than counting down through the second interval. In both cases a "borrow" signal will indicate the condition it is desired to detect, though for FIG. 3 its inverse is taken.

FIG. 3 shows two different frequency pulse sources 41 and 42 of which the first is slower than the second and is used via gate 43 to cause a reversible counter 44 to count up at the slower rate during one R pulse interval, for example as determined by the B output of the bistable 10 of FIG. 1. That bistable, the two counters 15 and 16 and gating from the pulse sources 17 and 18 is assumed to be represented in FIG. 3 by the block 40 which provides as output 26 the OR-ed borrow lines from those counters. In fact, the pulse sources 41 and 42 may be those 18 and 17 respectively of FIG. 1, though it will generally be preferred to use only the middle frequency one in common and to provide another variable higher frequency source to allow separate adjustment of the pulse ratio intervals that will be detected as short-before-long and long-before-short, respectively.

During the next R pulse interval, gate 45 will be enabled to cause decrementing of the counter 44 at the faster rate. Only where the first interval is longer than the second by a predetermined amount will the borrow output 46 of the counter 44 fail to be energised. An inversion bar 47 is shown in the line 46 to indicate that the line will go to a logic setting state only when the borrow line fails to be energised.

The overlapped pairs of successive pulse intervals are similarly tested by counter 48, gates 49 and 51 and the inverted borrow output 52 of the counter 48, all in a manner clear from the description of counter 16 of FIG. 1 and counter 44 of FIG. 3.

The inverted borrow outputs 46 and 52 are OR-ed together to drive the set input of a bistable 53 which, when set, provides a logic enabling signal on its output 54. This controls a gate 55 on a branch 56 from the R line used to clock the shift register 29 to pass an R pulse as input to the shift register only when a short interval is detected following a longer one. To ensure that the gate 55 knows the result of the condition test prior to clocking of the register 29, it may be preferred to include a short delay indicated by the dashed box 57.

The reversible ectopic counter 30 is also driven by the output of the gate 55. The bistable 53 is reset by the next detection of a short interval followed by a relatively long one, i.e. when the line 45 goes to a logic enabling state.

Muscle noise can cause a lack of registration between ectopic counting and the actual occurrence of ectopics. This can be avoided by gating the OR-ed counter borrow lines using the bistable outputs.

For a single ectopic it is desired that its detection by one of the counters 44 and 48 should allow passage of an R pulse to the input of shift register 29 and counter 30 before its detection by one of the counters 15 and 16 causes the R pulses to be cut off from the output of gate 55. It is convenient for the R pulses to have a significant duration. Then, if the OR gate fed by the lines 46 and 52 is clocked by the R pulse leading edges, the gate 55 will be enabled for an ectopic in time to pass part of the same R pulse to the shift register input.

Another counter could be used only for bursts of ectopics and be arranged to give an alarm when a predetermined number occur together.

Such a system will result in all ectopics being recorded by both the shift register 29 and the counter 30. It is independent of the shape of the ectopic waveform and thus will detect small ectopics that most analogue systems would miss being based on amplitude and/or width comparisons.

An optimum system might, however, include at least a simple waveform shape detector in order to locate those ectopics that (nearly) coincide with normal heart beats and are of very different shape.

Grossly distorted complexes, for example, with two significant successive opposite polarity excursions as shown in FIG. 2, can be detected using a relatively short duration for the R pulses. Then, both excursions of the ectopic could cause individual R pulses that would be very close together. A suitable detector could then be operated by that short interval after what would, in fact, be an already detected ectopic.

It is a compartively simple matter using the counters 15, 16 and 44, 46 to provide for triggering an alarm indicating a sustained relatively high or low level, or even stopping; for example by detecting the average levels achieved by the counters over a desired number of cycles. Simple cumulative summing could be used for such detection.

What I claim is:

1. Cardiac monitoring apparatus comprising means for detecting normal and/or ectopic complexes in an electrocardiogram waveform, and means for comparing the intervals between successive detected complexes, the means for comparing comprising binary counting means, means for causing the binary counting means to count at different rates during successive said intervals, and means responsive to the contents of the counting means for detecting that successive said intervals differ by more than a predetermined amount.

2. Apparatus according to claim 1, in which the means for detecting complexes includes bistable means switchable between its states by each said complex, and the counting means is reversible, being switched in counting direction by each switching of bistable means.

3. Apparatus according to claim 2, in which the counting means comprises two reversible binary counters so connected via gating means controlled by the bistable means as to count in opposite directions relative to each other, one direction being at one rate and the other at a second rate, with reversals of counting direction on occurrence of each said complex.

4. Apparatus according to claim 3, comprising a further pair of reversible binary counters also so connected as to count in opposite directions and at different rates for each direction with reversals of counting direction on occurrence of each said complex, the rates of counting being such that the first mentioned two counters and the further pair of counters indicate opposite sense different relationships between successive intervals.

5. Apparatus according to claim 4, comprising means for detecting ectopic indicating states of the first mentioned and further counters and means for counting the complexes occurring between these states.

6. Apparatus according to claim 3, wherein the means responsive to the counter contents includes gating means connected to the borrow outputs of the counter.

7. Apparatus according to claim 1, in which the binary counting means is reversible and is so connected as to count in different directions during successive said intervals at different rates, and the means for detecting that successive said intervals differ by more than a predetermined amount includes means responsive to occurrence of predetermined states of the counting means representing that successive interval durations differ by amounts greater than accounted for by differences between the counting rates.

8. Apparatus according to claim 1, further comprising shift register means so connected to the complex detecting means as to be clocked once for each said complex to store ectopic indications, and means for indicating that, at any one time, the shift register means contains more than a predetermined number of ectopic indications.

9. Cardiac monitoring apparatus comprising means for detecting normal and ectopic complexes in an electrocardiogram waveform, means for providing indications of which complexes are ectopic, shift register means so connected to the first mentioned means as to be clocked once for each electrocardiogram complex, whether ectopic or not, and so connected as to receive and store ectopic indications, and means for indicating that, at any one time, the shift register means contains more than a predetermined number of ectopic indications.

* * * * *